United States Patent [19]

Raspanti et al.

[11] Patent Number: 5,395,967
[45] Date of Patent: Mar. 7, 1995

[54] POLYQUATERNARY COMPOUNDS AND THE USE THEREOF AS DYE FIXERS

[75] Inventors: Giuseppe Raspanti; Marco Brena, both of Bergamo, Italy

[73] Assignee: 3V Inc., Weehawken, N.J.

[21] Appl. No.: 72,784

[22] Filed: Jun. 7, 1993

[51] Int. Cl.$^6$ .............................. G07C 233/05
[52] U.S. Cl. .................... 564/159; 564/153; 564/157; 564/158; 564/192; 8/586; 8/606
[58] Field of Search ............... 564/156, 159, 291, 292, 564/293, 290, 157, 152, 155; 8/606, 586

[56] References Cited

U.S. PATENT DOCUMENTS 4,728,337  3/1988  Abel et al. ........................ 8/606

FOREIGN PATENT DOCUMENTS 0225281  6/1987  European Pat. Off. .
2333012  6/1977  France .
2566414  12/1985  France .
2090877  7/1982  United Kingdom .

OTHER PUBLICATIONS

Achwal, Colourage, Jul. 1990, pp. 29–31, 37(13) (Chemical Abstract 114: 124436p), 199).

*Primary Examiner*—Shailendra Kumar
*Attorney, Agent, or Firm*—Griffin, Butler, Whisenhunt & Kurtossy

[57] ABSTRACT

Polyquaternary compounds, a process for the preparation thereof and the use thereof as adjuvants to improve the washing fastness of cellulose fabrics or fibres dyed with direct or reactive dyes.

1 Claim, No Drawings

POLYQUATERNARY COMPOUNDS AND THE USE THEREOF AS DYE FIXERS

The present invention relates to polyquaternary compounds and the use thereof as adjuvants to improve the washing fastness of cellulose fabrics or fibres dyed with direct or reactive dyes.

The compounds according to the present invention have the general formula (I)

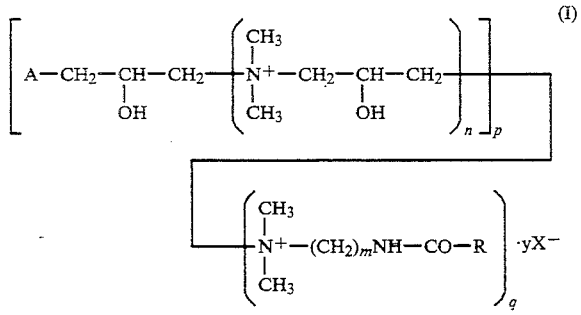

in which
n is an integer 1 to 20;
m is 2 or 3;
p is an integer 1 to 50;
q is 1 or 0;
y is an integer corresponding to the positive charges;
A is a group of formula (II) when p and q are both 1; is a group of formula (III) when p is higher than 1 and q is zero;

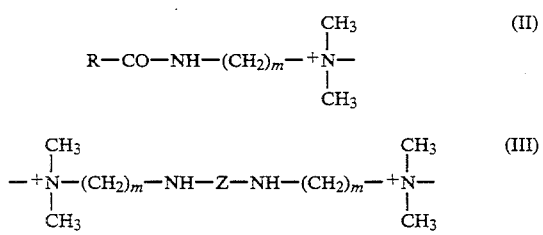

in which R is a $C_5$–$C_{19}$ straight or branched alkyl, cycloalkyl, aryl, aralkyl group;
Z is a carbonyl group or the diacyl residue of a dicarboxylic organic acid;
X is chlorine or bromine, preferably chlorine.

Examples of $C_5$–$C_{19}$ alkyl group comprise 1-ethylpentyl, n-hexyl, n-heptyl, n-decyl, n-undecyl, n-heptadecyl.

Examples of $C_5$–$C_{12}$ cycloalkyl comprise cyclopentyl and cyclohexyl.

Examples of aryl groups comprise phenyl and naphthyl, preferably phenyl.

Examples of aralkyl groups comprise benzyl and phenethyl.

A diacyl residue of a dicarboxylic acid is preferably the residue of a dicarboxylic aliphatic or aromatic acid, having 2 to 10 carbon atoms, such as ossalic, malonic, succinic, maleic, fumaric, suberic, sebacic, phthalic, terephthalic acids.

Preferred compounds of formula (I) are those in which n ranges 3 to 15 and m is 3, X is chlorine.

The polyquaternary compounds according to the present invention are prepared according to per se known methods, preferably by reacting dialkylants of formula (IV) with aminoamides of formulae (V) or (VI)

$$X-CH_2-CH-CH_2-\left[\underset{CH_3}{\underset{|}{\overset{CH_3}{\overset{|}{N}}}}-CH_2-CH-CH_2\right]_n^+ -X.nX^- \quad (IV)$$
$$\phantom{X-CH_2-}\underset{OH}{\phantom{|}}\phantom{-CH_2-}\underset{}{\phantom{|}}\phantom{-CH_2-CH-CH_2}\underset{OH}{\phantom{|}}$$

$$\underset{CH_3}{\underset{|}{\overset{CH_3}{\overset{|}{N}}}}-(CH_2)_m-NH-CO-R \quad (V)$$

$$\underset{CH_3}{\underset{|}{\overset{CH_3}{\overset{|}{N}}}}-(CH_2)_m-NH-Z-NH-(CH_2)_m-\underset{CH_3}{\underset{|}{\overset{CH_3}{\overset{|}{N}}}} \quad (VI)$$

in which n, m, R, Z, X have the meanings defined above. The intermediates (IV)–(VI) are known or are prepared according to known methods, for example as described respectively in FR 1,583,363, DOS 3,505,269, EP 225,282.

The reaction is carried out in polar solvents such as water, $C_1$–$C_3$ aliphatic alcohols, ethylene or propylene glycol, glycol monoalkyl ethers, such as monomethylpropylene glycol, monobutylene ethylene glycol, monomethyldiethylene glycol, acetonitrile, dimethylformamide or mixtures thereof. The reaction temperatures range from 20° C. to the boiling temperature of the solvent or of the solvent mixture used, preferably from 30° to 100° C.

The washing fastness of dyes or printings obtained by means of direct or reactive dyes is often insufficient. The unfixed dye remaining on the surface is removed slowly during the subsequent washings, thus resulting in fading of the dye and likelihood of staining other undyed material.

A number of attempts were carried out in order to overcome such a drawback, and an extensive patent literature exists on this subject. An attempt to solve this problem was made using reactive dyes which, as they form a chemical bond, show an excellent washing fastness. However, the use thereof requires many, abundant, laborious washings of the dyed material, to remove the portion of the dye that is hydrolysed and deposited on the fibre, which is therefore very expensive. A post-treatment of the dyed material with cationic adjuvants proved to be the most effective of all the proposed processes to improve the washing fastness. Among said adjuvants, satisfactory results were obtained with the products deriving from the condensation of cationic compounds with formic aldehyde. However, these products are dangerous from the toxicologic point of view, since they were proved to release continuously small amounts of formaldehyde, which is known to be very noxious, during the dye fixing process or even during the use of the dyed materials. As a consequence, such a class of compounds is still used very seldom. Other products which gave satisfactory results are the quaternary or cationic compounds deriving from the condensation of polyamines with cyanamide, dicyanodiamide, guanidine and an optional, subsequent reaction with epichlorohydrin. Nevertheless, the latter products suffer from fading: during the fixing process, the dye deposited on the fibres is partially released in the bath and therefore a decrease in the dye intensity (fading) takes place, moreover the dye released in the bath can stain any parts of the fabrics that are not dyed or dyed in pastel colours.

Surprisingly, the compounds of the present invention turned out to be very effective adjuvants to obtain dyes with excellent washing fastness without showing any fading.

According to the present invention, the post-treatment of the dyed cellulose fibres is effected immediately after the dyeing, but preferably with a fresh bath. The fibrous material can consists of celluloses, regenerated cellulose, viscose, flax, hemp, as well as mixtures of cotton with synthetic fibres, such as cotton/polyamide, cotton/polyester. The dyeing of the cellulose material can be carried out with direct or reactive dyes and with the foulard, printing or exhaustive processes. The improvements in the washing fastness is obtained, according to the present invention, mainly when using direct dyes and the exhaustive process.

The bath ratios can range from 1:5 to 1:50. The process is carried out at temperatures from 20° to 90° C., preferably from 30° to 60° C. The amounts of compounds of formula (I) necessary for the post-treatment range from 0.5 to 10%, preferably from 1 to 5% based on the weight of the dyed goods. The material treated with the adjuvants according to the present invention is subsequently dried at a temperature from 100° to 200° C. for a time ranging from 5 seconds to 10 minutes, depending on the drying temperature. Using the compounds of formula (I) as the fixers, excellent results are obtained concerning the washing fastness, the dry and humid fastnesses, the fastness to acid and alkali sweats, according to the methods UNI 7638/I, (III); UNI 5157 and UNI 7633.

The following Examples illustrate the present invention.

EXAMPLE 1

272 g of a 40% aqueous solution of the compound of formula (IV) (n=7, X=Cl) are added with 45 g of aminoamide of formula (V) (R=$C_7H_{15}$; m=3) and 197 g of water. The mixture is heated to 90° C. and stirred at this temperature for 4 hours. Compound of formula VII (n=7, R=$C_7H_{15}$) is obtained in form of a clear, colourless aqueous solution.

EXAMPLES 2–6

Following the procedure described in Example 1, the compounds listed in Table 1 are prepared.

TABLE 1

$$\text{R—CO—NH—(CH}_2)_3\text{—}^{+}\underset{\underset{CH_3}{|}}{\overset{\overset{CH_3}{|}}{N}}\text{—CH}_2\text{—}\underset{\underset{OH}{|}}{CH}\text{—CH}_2\text{—}\left[\underset{\underset{CH_3}{|}}{\overset{\overset{CH_3}{|}}{N}}\text{—CH}_2\text{—}\underset{\underset{OH}{|}}{CH}\text{—CH}_2\text{—}\right]_n^{+}\underset{\underset{CH_3}{|}}{\overset{\overset{CH_3}{|}}{N^+}}\text{—(CH}_2)_3\text{—NH—CO—R'(n+2)Cl}^{-} \quad \text{(VII)}$$

| Example | R | n |
|---|---|---|
| 2 | $C_4H_9$—CH(—$C_2H_5$)— | 7 |
| 3 | $C_{11}H_{25}$— | 3 |
| 4 | $C_6H_{13}$— | 10 |
| 5 | $C_7H_{15}$— | 15 |
| 6 | $C_{17}H_{35}$— | 3 |

EXAMPLE 7

375 g of a 40% aqueous solution of the dialkylant of formula (IV) (n=10, X=Cl) are added with 31 g of bis-(aminoamide) of formula (VI) (m=3, Z=—CO—(CH$_2$)$_4$—CO—) and 198 g of water. The reaction mixture is heated to 90° C. and stirred at this temperature for 4 hours, to obtain compound of formula VIII (n=10, Z=—CO—(CH$_2$)$_4$—CO—), in form of an aqueous solution.

EXAMPLES 8–12

Following the procedure described in Example 7, the compounds listed in Table 2 are prepared.

TABLE 2

$$\text{—}^{+}\underset{\underset{CH_3}{|}}{\overset{\overset{CH_3}{|}}{N}}\text{—(CH}_2)_3\text{—NH—Z—NH—(CH}_2)_3\text{—}^{+}\underset{\underset{CH_3}{|}}{\overset{\overset{CH_3}{|}}{N}}\text{—}\left[\text{CH}_2\text{—}\underset{\underset{OH}{|}}{CH}\text{—CH}_2\text{—}\underset{\underset{CH_3}{|}}{\overset{\overset{CH_3}{|}}{N}}\text{—}\right]_n^{+}\text{—CH}_2\text{—}\underset{\underset{OH}{|}}{CH}\text{—CH}_2\text{—}^{*}\text{(n+2)Cl}^{-} \quad \text{(VIII)}$$

| Example | Z | n |
|---|---|---|
| 8 | —CO—CO— | 7 |
| 9 | —CO—(CH$_2$)$_4$—CO— | 15 |
| 10 | —CO— | 10 |
| 11 | —CO—(CH$_2$)$_8$CO— | 5 |
| 12 | 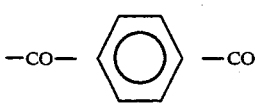 | 15 |

EXAMPLE 13

A cotton fabric is dyed by means of the exhaustive procedure in a 1:40 bath ratio in the presence of 20 g/l of sodium sulfate with 2.5% C.I. Direct Yellow 44 and 2.5 C.I. Direct Yellow 50. Portions of the dyed cotton are treated with the exhaustive process, heating to 40° C. for 20 minutes, in a 1:20 bath ratio with 3% (based on the treated good) of the compounds of formulae (VII), (VIII) and product C. Subsequently, the fastness tests are carried out on the rinsed, dried samples. Table 3 shows the results.

TABLE 3

| Example | Fading | Washing fastness |
|---------|--------|------------------|
| no adjuvant | 1 | 1 |
| 1 | 4 | 4–5 |
| 4 | 5 | 5 |
| 5 | 5 | 4–5 |
| 8 | 4–5 | 5 |
| 10 | 4 | 4–5 |
| *Product C | 2 | 4–5 |

Legenda:
1 means poor
5 means satisfactory
*Product C is the compound obtained condensing 1 mole of diethylenetriamine with 1 mole of dicyanodiamide according to DE-AS 1595390.

EXAMPLE 14

Following the procedure of Example 13, but dyeing the cotton with 2% C.I. Direct Blue 98 and 2% C.I. Direct Blue 71 and using 4% (based on the weight of the treated good) of fixing adjuvants. The results are reported in Table 4.

TABLE 4

| Example | Fading | Washing fastness |
|---------|--------|------------------|
| no adjuvant | 1 | 1 |
| 2 | 5 | 4–5 |

TABLE 4-continued

| Example | Fading | Washing fastness |
|---------|--------|------------------|
| 3 | 4–5 | 5 |
| 7 | 4–5 | 4–5 |
| 9 | 5 | 5 |
| 12 | 4–5 | 4–5 |
| *Product C | 2 | 4 |

We claim:
1. Compounds of general formula (I)

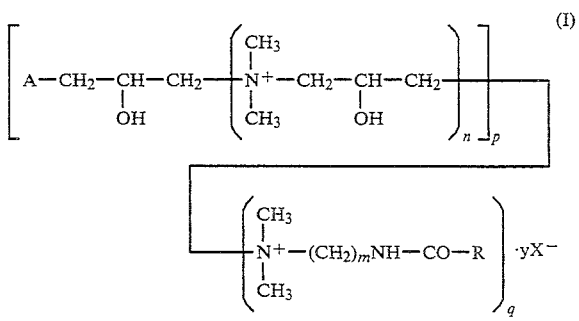

in which
n is an integer 1 to 20;
m is 2 or 3;
y is an integer corresponding to the positive charges;
A is a group of formula (II) and p and q are both 1;

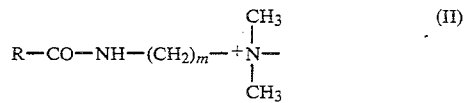

in which R is a $C_5$–$C_{19}$ straight or branched alkyl, cycloalkyl, aryl, aralkyl group;
X is chlorine or bromine.

* * * * *